United States Patent [19]
Yamamoto et al.

[11] Patent Number: 5,859,162
[45] Date of Patent: *Jan. 12, 1999

[54] SILICONE LADDER POLYMER AND PROCESS FOR PRODUCING THE SAME

[75] Inventors: Shigeyuki Yamamoto; Hiroyuki Nishimura; Hiroshi Adachi, all of Tokyo, Japan

[73] Assignee: Mitsubishi Denki Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 604,456

[22] Filed: Feb. 21, 1996

[30] Foreign Application Priority Data

Mar. 10, 1995 [JP] Japan ................................. 7-051202

[51] Int. Cl.[6] .................................................. C08G 77/06
[52] U.S. Cl. .............................................. 528/31; 528/10
[58] Field of Search ............................... 528/31, 10

[56] References Cited

U.S. PATENT DOCUMENTS

| | | | |
|---|---|---|---|
| 4,625,556 | 12/1986 | Nozue et al. | 522/99 |
| 4,626,556 | 12/1986 | Nozue et al. | 522/99 |
| 5,063,267 | 11/1991 | Hanneman et al. | 524/284 |
| 5,179,185 | 1/1993 | Yamamoto et al. | 528/32 |
| 5,183,846 | 2/1993 | Aiba et al. | 524/865 |
| 5,399,648 | 3/1995 | Yamamoto et al. | 528/12 |
| 5,416,190 | 5/1995 | Mine et al. | 528/492 |

FOREIGN PATENT DOCUMENTS 60-124943  4/1985  Japan .

OTHER PUBLICATIONS

Journal of The American Chemical Society 92:10, Sep. 23, 1970.

Journal of Polymer Science, 1963, vol. C–1.

*Primary Examiner*—Margaret W. Glass
*Attorney, Agent, or Firm*—Sughrue, Mion, Zinn, Macpeak & Seas, PLLC

[57] ABSTRACT

A high-purity silicone ladder polymer of high molecular weight which contains 1 ppm or less of sodium, potassium, iron, copper, lead, magnesium, manganese and chlorine, and 1 ppb or less of uranium and thorium; and whose polymerization degree is 600 to 10000. Trialkoxysilane compounds or trichlorosilane compounds are hydrolyzed to produce a high-purity silicone ladder prepolymer whose polymerization degree is 5 to 600. The silicone ladder prepolymer is subjected to dehydrative condensation by using a nucleophilic reagent as a catalyst, and then purified in a dissolution/reprecipitation method to yield the silicone ladder polymer.

5 Claims, No Drawings

SILICONE LADDER POLYMER AND PROCESS FOR PRODUCING THE SAME

BACKGROUND OF THE INVENTION

1. Field of the Invention

This invention relates to a high-purity silicone ladder polymer of high molecular weight having hydrogen atoms in side chains, a silicone ladder prepolymer, and processes for producing them. A silicone ladder polymer of the invention can be advantageously used as a material for making protective films, inter-level insulation films, etc in semiconductors and other electronic devices.

2. Description of the Prior Art

Because of its unique molecular structure, a silicone ladder polymer excels in heat resistance, electrical insulating properties and chemical resistance. It have been conventionally been used as a material for making protective films and inter-level insulation films in electronic parts or semiconductor devices, etc.

For example, a conventional process for producing such a conventional silicone ladder polymer is described in Japan Patent Laid-open (Kokai) No. 124943/85. In this process, triethoxysilane is hydrolyzed in an organic solution and polymerized under a reduced pressure. The terminal thereof is modified with dimethylchlorosilane. The resultant is then purified with an organic solvent to yield a silicone ladder polymer.

The conventional process for producing a silicone ladder polymer had a problem that a silicone ladder polymer obtained contained large amounts of impurities or by-products. This is because the purification after modifying a terminal is not sufficient and the reaction after hydrolysis is conducted under conditions where impurities or by-products are hardly removed, e.g., at a high temperature of 35° C. Further, since the molecular weight of the silicone ladder polymer obtained is as low as 100000 or less, there is another problem that the formation of a thick film is difficult.

SUMMARY OF THE INVENTION

An object of the invention is to provide a high-purity silicone ladder polymer of high molecular weight.

Another object thereof is to provide a high-purity silicone ladder prepolymer for use in producing the silicone ladder polymer.

A further object thereof is to provide a process for producing a high-purity silicone ladder prepolymer.

A further object thereof is to provide a process for producing a high-purity silicone ladder polymer of high molecular weight.

A silicone ladder polymer as a preferable embodiment of the invention is characterized by containing 1 ppm or less of sodium, potassium, iron, copper, lead, magnesium, manganese and chlorine, and 1 ppb or less of uranium and thorium; and being represented by a formula (1),

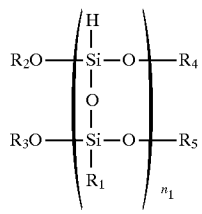

wherein $R_1$ represents a hydrogen atom, a lower alkyl group, an alkenyl group which may be substituted or an aryl group; $R_2$, $R_3$, $R_4$ and $R_5$ represent a hydrogen atom or a lower alkyl group; and $n_1$ represents a natural number of 600 to 10000.

As a silicone ladder prepolymer as a preferable embodiment of the invention is characterized by containing 1 ppm or less of sodium, potassium, iron, copper, lead, magnesium, manganese and chlorine, and 1 ppb or less of uranium and thorium; and being represented by a formula (2),

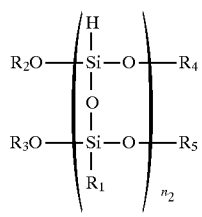

wherein $R_1$ represents a hydrogen atom, a lower alkyl group, an alkenyl group which may be substituted or an aryl group; $R_2$, $R_3$, $R_4$ and $R_5$ represent a hydrogen atom or a lower alkyl group; and $n_2$ represents a natural number of 5 to 600.

A process for producing the silicone ladder prepolymer as a preferable embodiment of the invention is characterized by comprising: dissolving a trialkoxysilane compound of a formula (3),

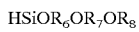

$$HSiOR_6OR_7OR_8$$

wherein $R_6$, $R_7$ and $R_8$ represent a lower alkyl group; or this compound and a trialkoxysilane compound of a formula (4),

$$R_9SiOR_6OR_7OR_8$$

wherein $R_9$ represents a lower alkyl group, an alkenyl group which may be substituted or an aryl group, and $R_6$, $R_7$ and $R_8$ represent a lower alkyl group in an organic solvent to produce a solution; hydrolyzing the solution with ultrapure water containing hydrogen chloride under cooling to produce a hydrolyzate; and washing the hydrolyzate with ultrapure water.

A process for producing the silicone ladder prepolymer as a preferable embodiment of the invention is characterized by comprising: dissolving a trichlorosilane compound of a formula (5), $HSiCl_3$; or this compound and a trichlorosilane compound of a formula (6),

$$R_9SiOCl_3$$

wherein $R_9$ represents a lower alkyl group, an alkenyl group which may be substituted or an aryl group in an organic solvent to produce a solution; hydrolyzing the solution with ultrapure water under cooling to produce a hydrolyzate; and washing the hydrolyzate with ultrapure water.

A process for producing a silicone ladder prepolymer as a preferable embodiment of the invention is characterized in that the trialkoxysilane compound of the formula (3); or the trialkoxysilane compound of the formula (3) and the trialkoxysilane compound of the formula (4) are dissolved in the solution in such a way that a concentration of the silicone ladder prepolymer obtained in the solution can be 0.01 to 0.3 g/ml.

A process for producing a silicone ladder prepolymer as a preferable embodiment of the invention is characterized in that the trichlorosilane compound of the formula (5); or the trichlorosilane compound of the formula (5) and the trichlorosilane compound of the formula (6) are dissolved in the solution in such a way that a concentration of the silicone ladder prepolymer obtained in the solution can be 0.01 to 0.3 g/ml.

A process for producing a silicone ladder prepolymer as a preferable embodiment of the invention is characterized in that a reaction temperature of the hydrolysis ranges from −30° C. to 30° C.

A process for producing the silicone ladder polymer as a preferable embodiment of the invention is characterized by comprising: adding a nucleophilic reagent to an organic solvent solution of the silicone ladder prepolymer to initiate dehydrative condensation to yield a product of high molecular weight; and purifying the product by a dissolution/reprecipitation method.

Preparation of Silicone Ladder Prepolymers

First, starting compounds will be explained.

In the first process for producing a silicone ladder prepolymer, a trialkoxysilane compound of the formula (3), $HSiOR_6OR_7OR_8$ wherein $R_6$, $R_7$ and $R_8$ represent a lower alkyl group; and a trialkoxysilane compound of the formula (4), $R_9SiOR_6OR_7OR_8$ wherein $R_9$ represents a lower alkyl group, an alkenyl group which may be substituted or an aryl group, and $R_6$, $R_7$ and $R_8$ represent a lower alkyl group are used as a starting compound. It is desirable to use trialkoxysilane compounds which have been already purified by distillation in a nitrogen stream under a reduced pressure. These starting trialkoxysilane compounds have the low reactivity with moisture and are not likely to change upon standing in the atmosphere. However, they are also characterized by low likelihood for hydrolysis and polycondensation.

A trialkoxysilane compound of the formula (3), $HSiOR_6OR_7OR_8$ wherein $R_6$, $R_7$ and $R_8$ represent a lower alkyl group is exemplified by, but not limited to, trimethoxysilane, triethoxysilane and tripropoxysiiane.

A trialkoxysilane compound of the formula (4), $R_9SiOR_6OR_7OR_8$ wherein $R_9$ represents a lower alkyl group, an alkenyl group which may be substituted or an aryl group, and $R_6$, $R_7$ and $R_8$ represent a lower alkyl group is exemplified by, but not limited to, phenyltrimethoxysilane, phenyltriethoxysilane, phenyltripropoxysilane, 2-phenylvinyltrimethoxysilane, 2-phenyvinyltriethoxysilane, 2-phenylvinyltripropoxysilane, 3-phenylallyltrimethoxysilane, 3-phenylallyltriethoxysilane, 3-phenylallyltripropoxysilane, vinyltrimethoxysilane, vinyltriethoxysilane, vinyltripropoxysilane, allyltrimethoxysilane, allyltriethoxysilane, allyltripropoxysilane, methyltrimethoxysilane, methyltriethoxysilane, methyltripropoxysilane, ethyltrimethoxysilane, ethyltriethoxysilane, ethyltripropoxysilane, n-propyltrimethoxysilane, n-propyltriethoxysilane, and n-propyltripropoxysilane.

In the second process for producing a silicone ladder prepolymer, a trichlorosilane compound of the formula (5), $HSiCl_3$; and a trichlorosilane compound of the formula (6), $R_9SiCl_3$ wherein $R_9$ represents a lower alkyl group, an alkenyl group which may be substituted or an aryl group are used as a starting compound. It is desirable to use trichlorosilane compounds which have been already purified by distillation in a nitrogen stream under a reduced pressure. The purified trichlorosilane compounds readily hydrolyze in the presence of atmospheric moisture, thereby generating hydrogen chloride to become silica. Hence, it is recommended to handle the trichlorosilane compounds with care to avoid contact with moisture containing air.

Next, reaction conditions will be explained.

In the first step, a trialkoxysilane compound of the formula (3); a trialkoxysilane compound of the formula (3) and a trialkoxysilane compound of the formula (4); a trichlorosilane compound of the formula (5); or a trichlorosilane compound of the formula (5) and a trichlorosilane compound of the formula (6) are dissolved in an organic solvent to give a solution. The concentration thereof in the solution is preferably adjusted in such a way that the concentration of a silicone ladder prepolymer to be obtained in the organic solvent solution range from 0.01 to 0.3 g/ml. If the concentration of a silicone ladder prepolymer less than 0.01 g/ml, the rate of polymerization reaction is very slow and the molecular weight of the prepolymer obtained is low. Thus, after quenching the reaction, the organic solvent solution containing a hydrolyzate does not readily separate into an organic layer and an aqueous layer. If the concentration of the prepolymer exceeds 0.3 g/ml, heat generated during the hydrolysis is not effectively dissipated. Thus, the polymerization rate partially changes, whereby irregular structures may be introduced into the prepolymer.

As an organic solvent in which the trialkoxysilane compounds or trichlorosilane compounds are dissolved, non-aqueous organic solvents capable of dissolving the hydrolyzate may be used. Specific examples of such organic solvents include ketones such as methyl isobutyl ketone and methyl ethyl ketone; ethers such as diethyl ether and iopropyl ether; and aromatic hydorcarbons such as xylene, toluene and benzene. Among these solvents, electronic-grade (EL grade) chemicals of high purity are preferred and they can be used individually or in admixtures.

In the first process, ultrapure water containing hydrogen chloride is added dropwise to an organic solvent solution in which trialkoxysilane compounds of the formulas (3) and (4) are dissolved, under cooling. As ultrapure water, pure water is used from which impurities have been removed as much as possible and which has a specific resistance of 16MΩ·cm or above. The ultrapure water containing hydrogen chloride means pure water which contains 0.02 to 0.23 mole of hydrogen chloride (EL grade) per mole of a mixture of starting compounds represented by the formula (3) and (4). If the concentration of hydrogen chloride is less than 0.02 mole, hydrogen chloride cannot sufficiently serve as a catalyst so that the reaction rate is slow. If the concentration exceeds 0.23 mole, not only is it impossible for the catalyst to exhibit the intended effect that is commensurate with its amount but it also has the tendency to impede the progress of the reaction.

In the second process, ultrapure water is added dropwise to an organic solvent solution in which trichlorosilane compounds of the formulas (5) and (6) are dissolved, under cooling. The ultrapure water may or may not contain hydrogen chloride. The ultrapure water is preferably added in an amount of 0.5 to 2.0 mole per mole of a starting material.

In the first and second precesses, when cooling the organic solvent solution, the temperature of the solution is preferably adjusted to between −30° C. and 30° C., more preferably between −20° C. and 25° C. If the temperature is lower than −30° C., the added ultrapure water solidifies to prevent the effective progress of hydrolysis. If the temperature is higher than 30° C., the evaporation of the added hydrogen chloride is accelerated and hydrolysis does not proceed rapidly enough. After the dropwise addition of ultrapure water ends, stirring is preferably continued for an additional 2 to 5 hours in order to bring the hydrolytic reaction to completion.

After the end of the reaction, the reaction solution is separated into two layers, or an organic solvent layer and an aqueous layer.

Next, the lower aqueous layer is removed by a suitable means such as a separating funnel and the organic solvent layer containing a silicone ladder prepolymer is recovered. The recovered organic solvent layer is then washed with ultrapure water. Washing with ultrapure water in the invention may be implemented by various known methods. To give an example, the organic solvent layer is mixed with an equal volume of the above ultrapure water, the mixture is stirred or shaken and, thereafter, an organic layer is recovered. If this procedure is repeated three times or more, not only sodium and potassium ions but also chloride ion which occurs in a large amount can readily be removed from the silicone ladder prepolymer. It appears that these impurities can be removed since the prepolymer has a ladder structure which serves as a substantial barrier against the incorporation of impurities into the molecule. Further, the molecular weight of this prepolymer is low and thereby it cannot be recovered by a usual precipitation method with a suitable solvent. Thus, the prepolymer is preferably recovered as a powder by distilling off the solvent to sufficient dryness.

In the manner described above, there is recovered a silicone ladder prepolymer of the formula (2) which contains 1 ppm or less of sodium, potassium, iron, copper, lead, magnesium, manganese and chlorine, and 1 ppb or less of uranium and thorium; and whose polymerization degree (n) is 5 to 600.

Preparation of High-Purity Silicone Ladder Polymer of High Molecular Weight

The organic solvent solution containing the silicone ladder prepolymer, or in the case where the silicone ladder prepolymer is recovered as a powder, a solution obtained by dissolving the silicone ladder prepolymer in an organic solvent is transferred into, for example, a quartz glass flask equipped with a Teflon stirring rod, a reflux condenser and a Dean-Stark trap. Next, a nucleophilic reagent is put into the flask and the mixture is heated to initiate dehydrative condensation. The resulting product with an increased molecular weight is purified by a dissolution/reprecipitation method to yield a high-purity silicone ladder polymer with the polymerization degree (n) of 600 to 10000 represented by the formula (1).

As an organic solvent, nonaqueous organic solvents capable of dissolving a powderous prepolymer may be used. Specific examples of such organic solvents include: ketones such as methyl isobutyl ketone and methyl ethyl ketone; ethers such as diethyl ether and isopropyl ether; and aromatic hydrocarbons such as xylene, toluene and benzene. Among these solvents, electronic-grade chemicals (EL grade) of high purity are preferred and it is also preferred to use them either individually or in admixtures.

The nucleophilic reagent may be exemplified by hydroxides of elements such as K, Na and Cs. Preferably, EL-grade potassium hydroxide, sodium hydroxide, etc, are used. the nucleophilic reagent is preferably used in an amount of 0.01 to 5 weight %, more preferably 0.05 to 3 weight % of the silicone ladder prepolymer. If less than 0.01 weight % of the nucleophilic reagent is used, the catalyst activity is reduced to lower the rate of reaction involving the silicone ladder prepolymer. If more than 5 weight % of the nucleophilic reagent is used, the dissociation of siloxane bonds that form in the present of the nucleophilic reagent preferentially proceed, thereby reducing polymerization.

Then, the silicone ladder prepolymer is subjected to dehydrative condensation under heating in the organic solvent to which the nucleophilic reagent has been added. The heating time id preferably at least 1 hour. If the heating time is shorter than 1 hour, the reaction may not progress.

As a result of the dehydrative condensation, a silicone ladder polymer with the polymerization degree (n) of 600 to 10000 represented by the formula (1) can be obtained. The polymerization degree (n) of the polymer can be adjusted by selecting a kind and amount of the solvent and catalyst, and time of the condensation reaction.

Since the silicone ladder polymer thus produced contains a small amount of the nucleophilic reagent as an impurity, the polymer is subsequently purified by a dissolution/reprecipitation method. The term "dissolution/reprecipitation method" as used herein means a method of purification in which an impurity-containing substance is dissolved in a good solvent and the resulting solution is gradually added in drops to a poor solvent to cause reprecipitation. An ether-base solvent can advantageously be used as a good solvent in the invention. A typical example of the good solvent is tetrahydrofuran. It is preferred to use a good solvent that has already been distilled, followed by filtration through a filter having a pore size of 0.5 μm. An alcoholic solvent can advantageously be used as a poor solvent in the invention. A typical example of the poor solvent is methyl alcohol. It is desirable to use a high-purity poor solvent of an EL grade.

The good solvent is added to the reaction solution containing the silicone ladder polymer in such an amount that the concentration of the polymer is within the range 2 to 15 weight %. If the concentration of the polymer is less than 2 weight %, the polymer does not readily reprecipitate and hence purification becomes difficult. Beyond 15 weight %, the concentration of the polymer is so high that the chance of the nucleophilic reagent of being trapped between molecules of the polymer increases, making it rather difficult for the polymer to be purified by reprecipitation.

The reaction solution containing the silicone ladder polymer to which the good solvent has been added is added in drops to the poor solvent. At this time, the volume of the poor solvent is preferably 5 to 20 times the volume of the reaction solution. If the volume of the poor solvent is less than 5 times the volume of the reaction solution, it is difficult to remove impurity ions. If the volume of the poor solvent exceeds 20 times the volume of the reaction solution, the solvent is simply wasted. The good solvent is gradually added in drops in order to achieve efficient removal of impurity ions.

The silicone ladder polymer that has been thus recovered by precipitation through addition to the poor solvent is further dissolved in the good solvent and then added dropwise to the poor solvent as mentioned above. As a result, the polymer is again recovered as a precipitate. If this procedure of purification is repeated 3 to 5 times, the content of the nucleophilic reagent is reduced to 1 ppm or less.

When the silicone ladder polymer thus obtained is analyzed by infrared spectrophotometry, absorption peaks were observed at 1135 cm$^{-1}$ and 1045 cm$^{-1}$. These peaks are assignable to the asymmetric stretching vibration of Si—O—Si which shows that the polymer has a ladder structure. It can be therefore verified that this polymer is a silicone ladder polymer.

The weight average molecular weight of this silicone ladder polymer is as high as 100,000 and more.

Accordingly, a high-purity silicone ladder polymer of high molecular weight can be produced which contains 1 ppm or less of sodium, potassium, iron, copper, lead, magnesium, manganese and chlorine, and 1 ppb or less of uranium and thorium; whose polymerization degree (n) is 600 to 10000, and which is represented by a formula (1).

The silicone ladder polymer is suitable for use in surface protective films, inter-level insulation films and the like in semiconductors, increasing the reliability of semiconductor elements.

DETAILED DESCRIPTION OF THE PREFERRED EMBODIMENTS

Examples 1–7

Various trialkoxysilane compounds of a kind (a) (formula (3)) and trialkoxysilane compounds of a kind (b) (formula (4)) listed in Table 1 were distilled under a reduced pressure in a nitrogen stream. They were dissolved in certain amounts of organic solvents of an EL grade listed in Table 1 to prepare solutions. Each of the solutions was transferred to a 2L four-neck flask equipped with a dripping funnel, a thermometer and a stirring rod. The solution was then cooled to a temperature (hydrolysis temperature) listed in Table 1. Under cooling and stirring, a certain amount of ultrapure water containing hydrogen chloride listed in Table 1 was gradually added in drops. At this time, heat generation was not vigorous and the addition was continued for 1 to 2 hours. After the addition, the reaction mixture was stirred for an additional 3 hours until the hydrolysis reaction was completed, thereby yielding a silicone ladder prepolymer.

This prepolymer solution was transferred to a separation funnel for separation into tow layers. The lower aqueous layer was removed and the organic layer containing the silicone ladder prepolymer was recovered. Ultrapure water, whose volume is equal to that of the organic layer, was added to the organic layer for washing under shaking. The same procedure was repeated 5 times. The washed silicone ladder prepolymer was analyzed for various impurity contents by an ion chromatographic analyzer (IC-500 of Yokogawa-Hokushin Electric Co., Ltd.). In each of Examples 1–7, the content of chloride ions in the silicone ladder prepolymer was 1,000 ppm after first washing, and it was 1 ppm or less after third washing. The concentration of potassium ions also decreased as the number of washings increased. It was 1 ppm or less after third washing. Various impurity contents in the silicone ladder prepolymers after third washing were shown in Table 2. As is apparent from Table 2, 1 ppm or less of sodium, potassium, iron, copper, lead, magnesium, manganese and chlorine, and 1 ppb or less of uranium and thorium were contained as impurities in the silicone ladder prepolymers.

Each concentration of sodium ions, potassium ions, iron ions, copper ions, lead ions, magnesium ions, and manganese ions was analyzed by an atomic-absorption analyzer (IC-500 of Shimazu Corp.). The concentration of chlorine ions was analyzed by an ion chromatographic analyzer (IC-500 of Yokogawa-Hokushin Electric Co., Ltd.). Each concentration of radioactive elements, uranium and thorium was analyzed by a fluorescence spectrophotometer (MPF-4 of Hitachi, Ltd.).

Next, the weight average molecular weights of the silicone ladder prepolymers obtained in Examples 1–7 were measured by a gel permeation chromatographic apparatus (TRI-ROTAR-IV of Hitachi Bunko K.K.). The results are shown in Table 2.

TABLE 1

| | Solvent | | Starting Compound | | | Hydrolysis Conditions | | |
|---|---|---|---|---|---|---|---|---|
| Ex. | Kind | Amount (ml) | Kind (a) | Kind (b) | Amount (a/b)g | Temp. (°C.) | Ultrapure water (ml) | HCl in mol. ratio |
| 1 | diethyl ether | 811 | triethoxy silane | ethyltri- ethoxysilane | 100/50 | −10 | 150 | 0.05 |
| 2 | toluene | 1000 | triethoxy silane | methyltri- ethoxysilane | 95/69 | −20 | 180 | 0.15 |
| 3 | methyl isobutyl ketone | 900 | triethoxy silane | | 100/0 | −20 | 210 | 0.02 |
| 4 | xylene | 1600 | triethoxy silane | n-propyltri- ethoxysilane | 50/105 | 5 | 150 | 0.08 |
| 5 | benzene | 830 | triethoxy silane | phenyltri- ethoxysilane | 120/60 | 0 | 170 | 0.23 |
| 6 | xylene | 790 | triethoxy silane | vinyltri- ethoxysilane | 80/75 | 10 | 300 | 0.12 |
| 7 | methyl isobutyl ketone | 670 | triethoxy silane | ethyltri- ethoxysilane | 125/25 | 25 | 250 | 0.2 |

TABLE 2

| | Weight Average | Impurity Content | | | | | | | | | |
|---|---|---|---|---|---|---|---|---|---|---|---|
| | | ppm | | | | | | | | ppb | |
| Ex. | Molecular Weight | Na | K | Cl | Fe | Cu | Pb | Mg | Mn | U | Th |
| 1 | 9300 | 0.98 | 0.95 | 0.74 | ≦0.8 | ≦0.8 | ≦0.8 | ≦0.8 | ≦0.8 | ≦1 | ≦1 |
| 2 | 12000 | 0.75 | 0.89 | 0.79 | ≦0.8 | ≦0.8 | ≦0.8 | ≦0.8 | ≦0.8 | ≦1 | ≦1 |
| 3 | 2000 | 0.91 | 0.97 | 0.92 | ≦0.8 | ≦0.8 | ≦0.8 | ≦0.8 | ≦0.8 | ≦1 | ≦1 |
| 4 | 13600 | 0.88 | 0.84 | 0.89 | ≦0.8 | ≦0.8 | ≦0.8 | ≦0.8 | ≦0.8 | ≦1 | ≦1 |
| 5 | 8700 | 0.79 | 0.78 | 0.76 | ≦0.8 | ≦0.8 | ≦0.8 | ≦0.8 | ≦0.8 | ≦1 | ≦1 |
| 6 | 31000 | 0.74 | 0.88 | 0.79 | ≦0.8 | ≦0.8 | ≦0.8 | ≦0.8 | ≦0.8 | ≦1 | ≦1 |
| 7 | 9500 | 0.68 | 0.82 | 0.9 | ≦0.8 | ≦0.8 | ≦0.8 | ≦0.8 | ≦0.8 | ≦1 | ≦1 |

Further, the structures of the silicone ladder prepolymers obtained in Examples 1–7 were analyzed by an infrared spectrophotometry (FT/IR-111 of Hitachi Bunko K.K.). As a result, a double peak showing a siloxane bond was observed at near 1100 cm⁻(journal of Polymer Science, 1963, vol. C-1, page 83). Thus, it is verified that these silicone ladder polymers have a structure represented by the following formula (2);

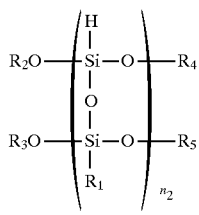

wherein $R_1$ represents a hydrogen atom, a lower alkyl group, an alkenyl group which may be substituted or an aryl group; $R_2$, $R_3$ $R_4$ and $R_5$ represent a hydrogen atom or a lower alkyl group; and $n_2$ represents a natural number of 5 to 600.

Comparative Examples 1–4

As in Examples 1–7, under reaction conditions listed in Table 3, trialkoxysilane compounds of kinds (a) and (b) were hydrolyzed. In Comparative Examples 1 and 3, since a hydrolysis temperature was as low as –50° C., ultrapure water solidified upon dropwise addition. Thus, hydrolysis did not proceed satisfactorily. The molecular weight of the prepolymer obtained was extremely low. In Comparative Examples 2 and 4, since a hydrolysis temperature was as high as 40° C., HCl which was added dropwise together with ultrapure water evaporated very rapidly. Thus, hydrolysis did not proceed satisfactorily. Consequently, reaction solutions could not be purified by washing with water.

TABLE 3

| | Solvent | | Starting Compound | | | Hydrolysis Conditions | | |
|---|---|---|---|---|---|---|---|---|
| Ex. | Kind | Amount (ml) | Kind (a) | Kind (b) | Amount (a/b)g | Temp. (°C.) | Ultrapure water (ml) | HCl in mol. ratio |
| 1 | xylene | 950 | triethoxysilane | ethyltriethoxysilane | 100/65 | –50 | 180 | 0.12 |
| 2 | diethyl ether | 700 | triethoxysilane | methyltriethoxysilane | 120/30 | 40 | 210 | 0.05 |
| 3 | xylene | 550 | triethoxysilane | ethyltriethoxysilane | 95/55 | –50 | 220 | 0.1 |
| 4 | methyl isobutyl ketone | 1250 | triethoxysilane | n-propyltriethoxysilane | 115/40 | 40 | 150 | 0.07 |

Examples 8–14

As in Examples 1–7, under reaction conditions listed in Table 4, certain amounts of trialkoxysilane compounds of kinds (a) and (b) were hydrolyzed to produce high-purity silicone ladder prepolymer.

Next, a solution containing the silicone ladder prepolymer was transferred into a 2 L four-neck quartz glass flask equipped with a Teflon stirring rod, a Dean-Stark trap and a thermometer. Further, a certain amount listed in Table 4 of a solution, which is obtained by dissolving KOH in an EL grade methanol to a concentration of 0.1 mg/ml, was put into the flask as a nucleophilic reagent. Dehydrative condensation reaction was carried out under heating at a temperature listed in Table 4 for a length of time listed in Table 4.

After the dehydrative condensation, the resulting solution was cooled. Then, purified tetrahydrofuran was added in such an amount that the content of a polymer component be a concentration listed in Table 5, and thoroughly stirred to prepare a solution. Subsequently, the solution was added dropwise to methyl alcohol (EL grade) in an amount 10 times. The resulting precipitate of a silicone ladder polymer having a high molecular weight was recovered. Further, the recovered precipitate was dried and tetrahydrofuran was again added to prepare a solution of the same concentration as used above. By similar precipitation, a silicone ladder polymer was recovered. This procedure was repeated four times.

For the silicone ladder polymer of high molecular weight thus synthesized, the weight average molecular weight; and each concentration of sodium ions, potassium ions, iron ions, copper ions, lead ions, magnesium ions, manganese ions, chlorine ions, uranium and thorium were measured as in Examples 1–7. These results are shown in Table 5. As is apparent from Table 5, a high-purity silicone ladder polymer was obtained. The concentrations of impurity ions decreased with the increase in the number of reprecipitations.

such an amount that the content of a polymer component be a concentration listed in Table 7, and thoroughly stirred to prepare a solution. Subsequently, the solution was added dropwise to methyl alcohol (EL grade) in an amount 10 times. The resulting precipitate of a silicone ladder polymer having a high molecular weight was recovered. Further, the

TABLE 4

| | Solvent | | Starting Compound | | | Hydrolysis Conditions | | | Condensation Conditions | |
|---|---|---|---|---|---|---|---|---|---|---|
| Ex. | Kind | Amount (ml) | Kind (a) | Kind (b) | Amount (a/b)g | Temp. (°C.) | Ultrapure water (ml) | HCl in mol. ratio | Reagent wt % | Heating time (h) | Temp. (°C.) |
| 8 | diethyl ether | 650 | triethoxy silane | methyltri-ethoxysilane | 80/80 | −20 | 160 | 0.05 | 1 | 10 | 40 |
| 9 | toluene | 1500 | triethoxy silane | methyltri-ethoxysilane | 100/10 | −5 | 150 | 0.02 | 0.2 | 5 | 80 |
| 10 | diethyl ether | 700 | triethoxy silane | n-propyltri-ethoxysilane | 125/80 | 0 | 200 | 0.23 | 0.1 | 2 | 40 |
| 11 | methyl isobutyl ketone | 1000 | triethoxy silane | | 150/0 | −20 | 150 | 0.1 | 0.05 | 3 | 80 |
| 12 | toluene | 800 | triethoxy silane | phenyltri-ethoxysilane | 100/50 | 10 | 170 | 0.15 | 0.15 | 20 | 60 |
| 13 | xylene | 950 | triethoxy silane | vinyltri-ethoxysilane | 80/60 | −10 | 130 | 0.12 | 0.21 | 8 | 100 |
| 14 | methyl isobutyl ketone | 700 | triethoxy silane | ethyltri-ethoxysilane | 70/50 | 25 | 200 | 0.08 | 0.2 | 8 | 100 |

TABLE 5

| | | | Impurity Content | | | | | | | | |
|---|---|---|---|---|---|---|---|---|---|---|---|
| | Content | Weight Average | ppm | | | | | | | | ppb |
| Ex. | wt % | Molecular Weight | Na | K | Cl | Fe | Cu | Pb | Mg | Mn | U | Th |
| 8 | 12 | 684000 | 0.95 | 0.79 | 0.86 | ≦0.8 | ≦0.8 | ≦0.8 | ≦0.8 | ≦0.8 | ≦1 | ≦1 |
| 9 | 10 | 876000 | 0.69 | 0.91 | 0.87 | ≦0.8 | ≦0.8 | ≦0.8 | ≦0.8 | ≦0.8 | ≦1 | ≦1 |
| 10 | 2 | 196000 | 0.89 | 0.85 | 0.96 | ≦0.8 | ≦0.8 | ≦0.8 | ≦0.8 | ≦0.8 | ≦1 | ≦1 |
| 11 | 8 | 528000 | 0.82 | 0.98 | 0.92 | ≦0.8 | ≦0.8 | ≦0.8 | ≦0.8 | ≦0.8 | ≦1 | ≦1 |
| 12 | 10 | 129000 | 0.65 | 0.73 | 0.94 | ≦0.8 | ≦0.8 | ≦0.8 | ≦0.8 | ≦0.8 | ≦1 | ≦1 |
| 13 | 12 | 109000 | 0.87 | 0.89 | 0.81 | ≦0.8 | ≦0.8 | ≦0.8 | ≦0.8 | ≦0.8 | ≦1 | ≦1 |
| 14 | 15 | 351000 | 0.84 | 0.85 | 0.72 | ≦0.8 | ≦0.8 | ≦0.8 | ≦0.8 | ≦0.8 | ≦1 | ≦1 |

Examples 15–21

As in Examples 1–7, under reaction conditions listed in Table 6, certain amounts of trichlorosilane compounds of kinds (c) (formula (5)) and (d) (formula (6)) were hydrolyzed to produce high-purity silicone ladder prepolymer.

Next, a solution containing the silicone ladder prepolymer was transferred into a 2 L four-neck quartz glass flask equipped with a Teflon stirring rod, a Dean-Stark trap and a thermometer. Further, a certain amount listed in Table 4 of a solution, which is obtained by dissolving KOH in an EL grade methanol to a concentration of 0.1 mg/ml, was put into the flask as a nucleophilic reagent. Dehydrative condensation reaction was carried out under heating at a temperature listed in Table 6 for a time of period listed in Table 6.

After the dehydrative condensation, the resulting solution was cooled. Then, purified tetrahydrofuran was added in recovered precipitate was dried and tetrahydrofuran was again added to prepare a solution of the same concentration as used above. By similar precipitation, a silicone ladder polymer was recovered. This procedure was repeated four times.

For the silicone ladder polymer of high molecular weight thus synthesized, the weight average molecular weight; and each concentration of sodium ions, potassium ions, iron ions, copper ions, lead ions, magnesium ions, manganese ions, chlorine ions, uranium and thorium were measured as in Examples 1–7. These results are shown in Table 7. As is apparent from Table 7, a high-purity silicone ladder polymer was obtained. The concentrations of impurity ions decreased with the increase in the number of reprecipitations.

TABLE 6

| Comp. Ex. | Solvent Kind | Amount (ml) | Starting Compound Kind (c) | Kind (d) | Amount (c/d)g | Hydrolysis Conditions Temp. (°C.) | Ultrapure water (ml) | Condensation Conditions Reagent wt % | Heating time (h) | Temp. (°C.) |
|---|---|---|---|---|---|---|---|---|---|---|
| 15 | diethyl ether | 1000 | trichloro silane | methyltri-chlorosilane | 90/50 | −20 | 160 | 0.05 | 5 | 40 |
| 16 | toluene | 550 | trichloro silane | ethyltri-chlorosilane | 80/80 | −10 | 150 | 0.08 | 20 | 60 |
| 17 | methyl isobutyl ketone | 680 | trichloro silane | n-propyltri-chlorosilane | 125/80 | 0 | 200 | 3 | 10 | 80 |
| 18 | xylene | 1200 | trichloro silane | | 150/0 | −5 | 170 | 1.5 | 5 | 50 |
| 19 | benzene | 1500 | trichloro silane | phenyltri-chlorosilane | 100/50 | −10 | 190 | 1.2 | 2 | 60 |
| 20 | xylene | 820 | trichloro silane | vinyltri-chlorosilane | 80/60 | 10 | 250 | 0.07 | 10 | reflux |
| 21 | toluene | 670 | trichloro silane | ethyltri-chlorosilane | 130/100 | 25 | 155 | 0.2 | 10 | 50 |

TABLE 7

| Ex. | Content wt % | Weight Average Molecular Weight | Impurity Content ppm Na | K | Cl | Fe | Cu | Pb | Mg | Mn | ppb U | Th |
|---|---|---|---|---|---|---|---|---|---|---|---|---|
| 15 | 15 | 684000 | 0.74 | 0.72 | 0.85 | ≦0.8 | ≦0.8 | ≦0.8 | ≦0.8 | ≦0.8 | ≦1 | ≦1 |
| 16 | 10 | 521000 | 0.95 | 0.95 | 0.92 | ≦0.8 | ≦0.8 | ≦0.8 | ≦0.8 | ≦0.8 | ≦1 | ≦1 |
| 17 | 5 | 169000 | 0.92 | 0.81 | 0.68 | ≦0.8 | ≦0.8 | ≦0.8 | ≦0.8 | ≦0.8 | ≦1 | ≦1 |
| 18 | 2 | 465000 | 0.88 | 0.73 | 0.79 | ≦0.8 | ≦0.8 | ≦0.8 | ≦0.8 | ≦0.8 | ≦1 | ≦1 |
| 19 | 6 | 171000 | 0.69 | 0.85 | 0.76 | ≦0.8 | ≦0.8 | ≦0.8 | ≦0.8 | ≦0.8 | ≦1 | ≦1 |
| 20 | 8 | 109000 | 0.78 | 0.88 | 0.94 | ≦0.8 | ≦0.8 | ≦0.8 | ≦0.8 | ≦0.8 | ≦1 | ≦1 |
| 21 | 11 | 264000 | 0.9 | 0.82 | 0.88 | ≦0.8 | ≦0.8 | ≦0.8 | ≦0.8 | ≦0.8 | ≦1 | ≦1 |

Comparative Examples 5–8

As in Examples 1–7, under reaction conditions listed in Table 8, trichlorosilane compounds of kinds (c) and (d) were hydrolyzed. However, in Comparative Examples 5 and 6, since the amount of an organic solvent was too large relative to trichlorosilane compounds, a hydrolyzate obtained had only a low molecular weight. In Comparative Examples 7, since a hydrolysis temperature was too low, a hydrolyzate obtained similarly had only a low molecular weight. These hydrolyzates could not be purified by washing with water. Thus, KOH was added to the hydrolyzates remaining unpurified as a catalyst in an amount listed in Table 8. Dehydrative condensation reaction was then performed by heating for a specific length of time. Since the hydrolyzates slightly polymerized, they were purified by washing with water. However, as shown in Table 9, the contents of impurities were high.

TABLE 8

| Comp. Ex. | Solvent Kind | Amount (ml) | Starting Compound Kind (c) | Kind (d) | Amount (c/d)g | Hydrolysis Conditions Temp. (°C.) | Ultrapure water (ml) | Condensation Conditions Reagent wt % | Heating time (h) | Temp. (°C.) |
|---|---|---|---|---|---|---|---|---|---|---|
| 5 | xylene | 2000 | trichloro silane | methyltri-chlorosilane | 100/50 | −20 | 150 | 0.05 | 20 | 80 |
| 6 | diethyl ether | 1650 | trichloro silane | n-propyltri-chlorosilane | 150/100 | −30 | 120 | 0.15 | 5 | 40 |
| 7 | toluene | 950 | trichloro silane | n-propyltri-chlorosilane | 95/40 | −40 | 170 | 1 | 2 | 100 |
| 8 | methyl isobutyl ketone | 1200 | trichloro silane | ethyltri-chlorosilane | 80/40 | −30 | 210 | 1.5 | 10 | 100 |

TABLE 9

| Comp. Ex | Weight Average Molecular weight | Impurity Content | | | | | | | | | |
|---|---|---|---|---|---|---|---|---|---|---|---|
| | | ppm | | | | | | | | ppb | |
| | | Na | K | Cl | Fe | Cu | Pb | Mg | Mn | U | Th |
| 5 | 4600 | 0.98 | 3 | ≦1.5 | ≦0.9 | ≦0.9 | ≦0.9 | ≦0.9 | ≦0.9 | ≦1.5 | ≦1.5 |
| 6 | 8100 | 0.95 | 1.5 | ≦1.5 | ≦0.9 | ≦0.9 | ≦0.9 | ≦0.9 | ≦0.9 | ≦1.5 | ≦1.5 |
| 7 | 5100 | 0.97 | 2.1 | ≦1.5 | ≦0.9 | ≦0.9 | ≦0.9 | ≦0.9 | ≦0.9 | ≦1.5 | ≦1.5 |
| 8 | 4300 | 0.94 | 1.2 | ≦1.5 | ≦0.9 | ≦0.9 | ≦0.9 | ≦0.9 | ≦0.9 | ≦1.5 | ≦1.5 |

From the results as shown in Tables 1–9, it is found that, compared with Comparative Examples 1–8, according to Examples 1–21, high-purity silicone ladder prepolymers and high-purity silicone ladder polymers of high molecular weight can be obtained which prepolymers and polymers contain small contents of impurities such as sodium, potassium, iron, copper, lead, magnesium, manganese, chlorine, uranium and thorium.

What is claimed is:

1. A process for producing a high purity silicone ladder polymer containing 1 ppm or less of sodium, potassium, iron, copper, lead, magnesium, manganese and chlorine, and 1 ppb or less of uranium and thorium; the polymer being represented by a formula (1),

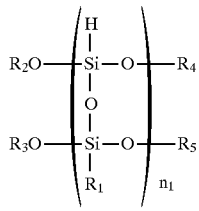

wherein $R_1$ represents a lower alkyl group an alkenyl group which is optionally substituted with an aryl group or an aryl group; $R_2$, $R_3$, $R_4$ and $R_5$ represent a hydrogen atom or a lower alkyl group; and $n_1$ represents a natural number of 600 to 10000, comprising the steps of:

adding a nucleophilic reagent to an organic solvent solution of a silicone ladder prepolymer comprising 1 ppm or less of sodium, potassium, iron, copper, lead, magnesium, manganese and chlorine, and 1 ppb or less of uranium and thorium; the prepolymer being represented by a formula (2),

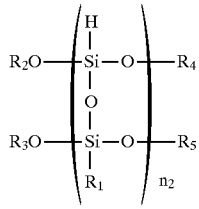

wherein $R_1$ represents a lower alkyl group, an alkenyl group which is optionally substituted with an aryl group or an aryl group; $R_2$, $R_3$, $R_4$ and $R_5$ represent a hydrogen atom or a lower alkyl group; and $n_2$ represents a natural number of 5 to 600 to initiate dehydrative condensation to yield a product of high molecular weight; and purifying the product by a dissolution/reprecipitation method.

2. A high purity silicone ladder polymer containing 1 ppm or less of sodium, potassium iron, copper, lead, magnesium, manganese and chlorine, and 1 ppb or less of uranium and thorium; the polymer being represented by a formula (1),

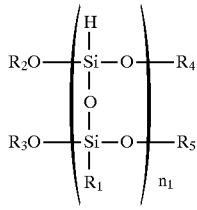

wherein $R_1$ represents a lower alkyl group, an alkenyl group which is optionally substituted with an aryl group or an aryl group; $R_2$, $R_3$, $R_4$ and $R_5$ represent a hydrogen atom or a lower alkyl group; and $n_1$ represents a natural number of 600 to 10000, said polymer having been prepared by the process of claim 1.

3. A process for producing a high purity silicone ladder prepolymer containing 1 ppm or less of sodium, potassium, iron, copper, lead, magnesium, manganese and chlorine, and 1 ppb or less of uranium and thorium; the prepolymer being represented by a formula (2),

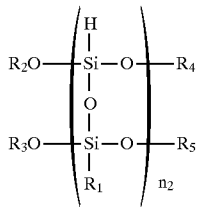

wherein $R_1$ represents a lower alkyl group, an alkenyl group which is optionally substituted with an aryl group or an aryl group; $R_2$, $R_3$, $R_4$ and $R_5$ represent a hydrogen atom or a lower alkyl group; and $n_2$ represents a natural number of 5 to 600, comprising the steps of:

dissolving a trialkoxysilane compound of formula (3),

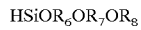

$HSiOR_6OR_7OR_8$ wherein $R_6$, $R_7$ and $R_8$ represent a lower alkyl group; or the trialkoxysilane compound of the formula (3) and a trialkoxysilane compound of formula (4),

$R_9SiOR_6OR_7OR_8$ wherein $R_9$ represents a lower alkyl group, an alkenyl group which is optionally substituted with an aryl group or an aryl group, and $R_6$, $R_7$ and $R_8$ represent a lower alkyl group in an organic solvent to produce a solution containing said prepolymer in a concentration of 0.01 to 0.3 g/ml;

hydrolyzing the solution at a temperature of −30° C. to 30° C. with pure water from which substantially all impurities have been removed to which hydrogen chloride has been added under cooling to produce a hydrolyzate; and washing the hydrolyzate with pure water from which substantially all impurities have been removed.

4. A process for producing a high purity silicone ladder prepolymer containing 1 ppm or less of sodium, potassium, iron, copper, lead, magnesium, manganese and chlorine, and 1 ppb or less of uranium and thorium; the prepolymer being represented by a formula (2),

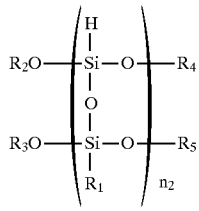

wherein $R_1$ represents a lower alkyl group, an alkenyl group which is optionally substituted with an aryl group or an aryl group; $R_2$, $R_3$, $R_4$ and $R_5$ represent a hydrogen atom or a lower alkyl group; and $n_2$ represents a natural number of 5 to 600, comprising the steps of:

dissolving a trichlorosilane compound of a formula (5), $HSiCl_3$; or the trichlorosilane compound of the formula (5) and a trichlorosilane compound of a formula (6),

$R_9SiCl_3$ wherein $R_9$ represents a lower alkyl group, an alkenyl group which is optionally substituted with an aryl group or an aryl group in an organic solvent to produce a solution containing said prepolymer in a concentration of 0.01 to 0.3 g/ml;

hydrolyzing the solution at a temperature of −30° C. to 30° C. with pure water from which substantially all impurities have been removed to which hydrogen chloride optionally has been added under cooling to produce a hydrolyzate; and washing the hydrolyzate with pure water from which substantially all impurities have been removed.

5. A high purity silicone ladder prepolymer containing 1 ppm or less of sodium, potassium, iron, copper, lead, magnesium, manganese and chlorine, and 1 ppb or less of uranium and thorium; the prepolymer being represented by a formula (2),

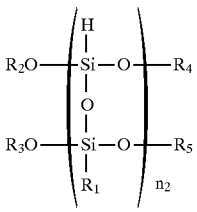

wherein $R_1$ represents a lower alkyl group, an alkenyl group which is optionally substituted with an aryl group or an aryl group; $R_2$, $R_3$, $R_4$ and $R_5$ represent a hydrogen atom or a lower alkyl group; and $n_2$ represents a natural number of 5 to 600, said prepolymer having been prepared by the process of claim 3 or 4.

* * * * *